United States Patent [19]

Weinstock et al.

[11] Patent Number: 5,639,276

[45] Date of Patent: Jun. 17, 1997

[54] DEVICE FOR USE IN RIGHT VENTRICULAR PLACEMENT AND METHOD FOR USING SAME

[75] Inventors: Barry S. Weinstock, Largo; Christopher C. Maxson, Tarpon Springs, both of Fla.

[73] Assignee: Rapid Development Systems, Inc., Largo, Fla.

[21] Appl. No.: 311,680

[22] Filed: Sep. 23, 1994

[51] Int. Cl.$^6$ .................................................. A61N 1/372
[52] U.S. Cl. .............................. 606/129; 607/122; 128/772
[58] Field of Search ..................... 606/129; 607/116, 607/122, 123; 604/264; 128/772

[56] References Cited

U.S. PATENT DOCUMENTS

| | | | |
|---|---|---|---|
| 3,448,739 | 6/1969 | Stark et al. | 128/2.05 |
| 3,746,003 | 7/1973 | Blake et al. | 128/349 B |
| 3,995,623 | 12/1976 | Blake et al. | 128/2.06 E |
| 4,010,755 | 3/1977 | Preston | 128/404 |
| 4,166,469 | 9/1979 | Littleford | 128/748 |
| 4,215,703 | 8/1980 | Willson | 128/772 |
| 4,243,050 | 1/1981 | Littleford | 128/784 |
| 4,328,806 | 5/1982 | Cooper | 128/349 B |
| 4,329,993 | 5/1982 | Lieber et al. | 128/349 B |
| 4,329,994 | 5/1982 | Cooper | 128/349 B |
| 4,467,817 | 8/1984 | Harris | 128/786 |
| 4,602,645 | 7/1986 | Barrington et al. | 128/786 |
| 4,651,751 | 3/1987 | Swendson et al. | 128/786 |
| 4,664,120 | 5/1987 | Hess | 607/123 |
| 4,676,249 | 6/1987 | Arenas et al. | 128/772 |
| 4,717,381 | 1/1988 | Papantonakos | 605/95 |
| 4,721,118 | 1/1988 | Harris | 128/785 |
| 4,917,102 | 4/1990 | Miller et al. | 128/772 |
| 5,098,392 | 3/1992 | Fleischhacker et al. | 604/165 |
| 5,099,839 | 3/1992 | Miyata et al. | 607/122 |
| 5,246,014 | 9/1993 | Williams et al. | 607/122 |
| 5,409,469 | 4/1995 | Schaerf | 604/282 |

FOREIGN PATENT DOCUMENTS 0 219 608  6/1986  European Pat. Off. .

OTHER PUBLICATIONS

Cook Incorporated Catalog, "Peel Away", pp. 1–4. Mar. 1979.

*Primary Examiner*—Sam Rimell
*Assistant Examiner*—Benjamin Koo
*Attorney, Agent, or Firm*—Burns, Doane, Swecker & Mathis L.L.P.

[57] ABSTRACT

A device and method for rapid, atraumatic placement of medical devices in the right ventricle of a patient. The device includes an introducer sheath used as a passage for intravenous placement of a medical device in a patient's heart. The introducer sheath is of sufficient length to allow a proximal end thereof to be located outwardly from an incision in the skin of a patient over the cephalic vein when a distal end of the introducer sheath is at the apex of the right ventricle. The introducer sheath is of sufficient flexibility to pass through the tricuspid valve and through the narrow passage between the clavicle and first rib, and is of sufficient strength to allow the introducer sheath to be pushed along its length thereof through the tortuous path from the incision over the cephalic vein to the apex of the right ventricle. The introducer sheath has an inside diameter of sufficient size to slidably receive a balloon-tipped catheter, a guidewire, a pacing lead, or the like therein.

74 Claims, 8 Drawing Sheets

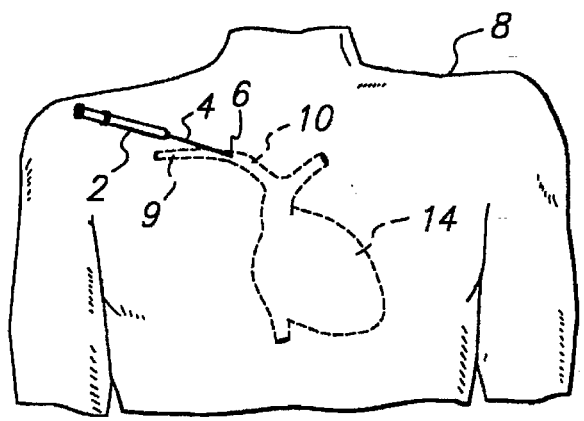
FIG. 1
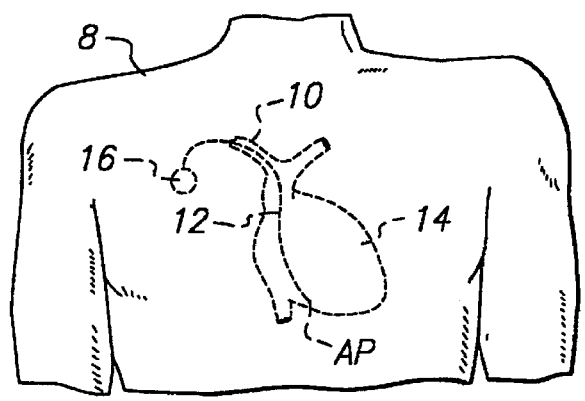
FIG. 2
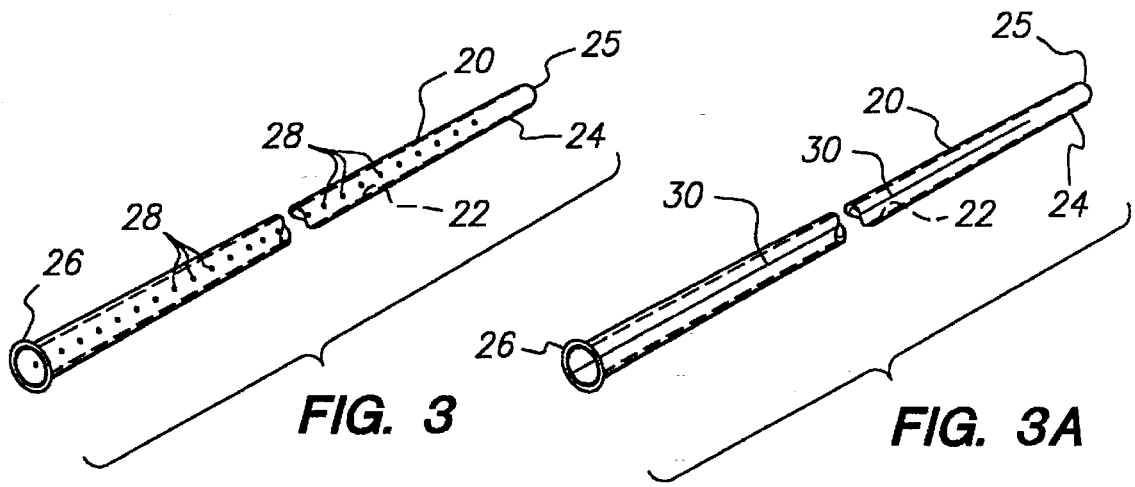
FIG. 3   FIG. 3A

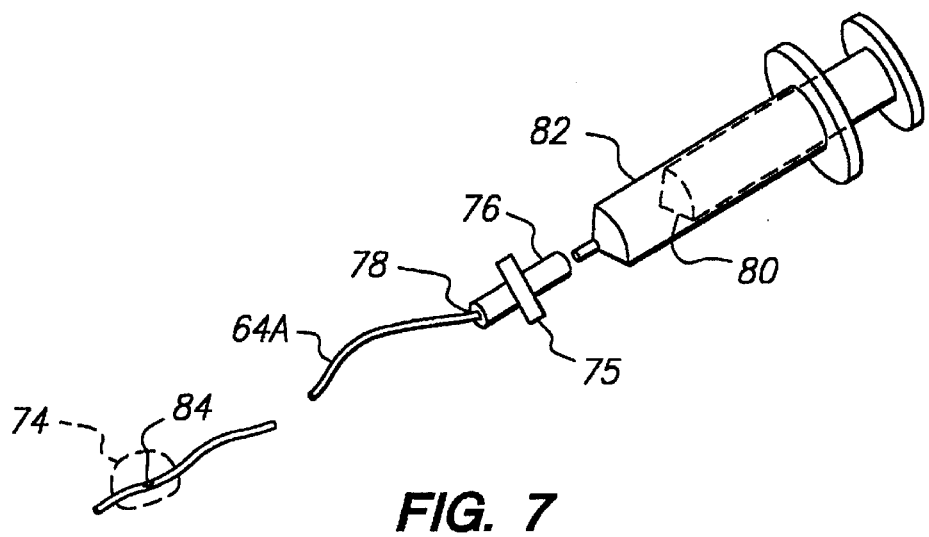
FIG. 7
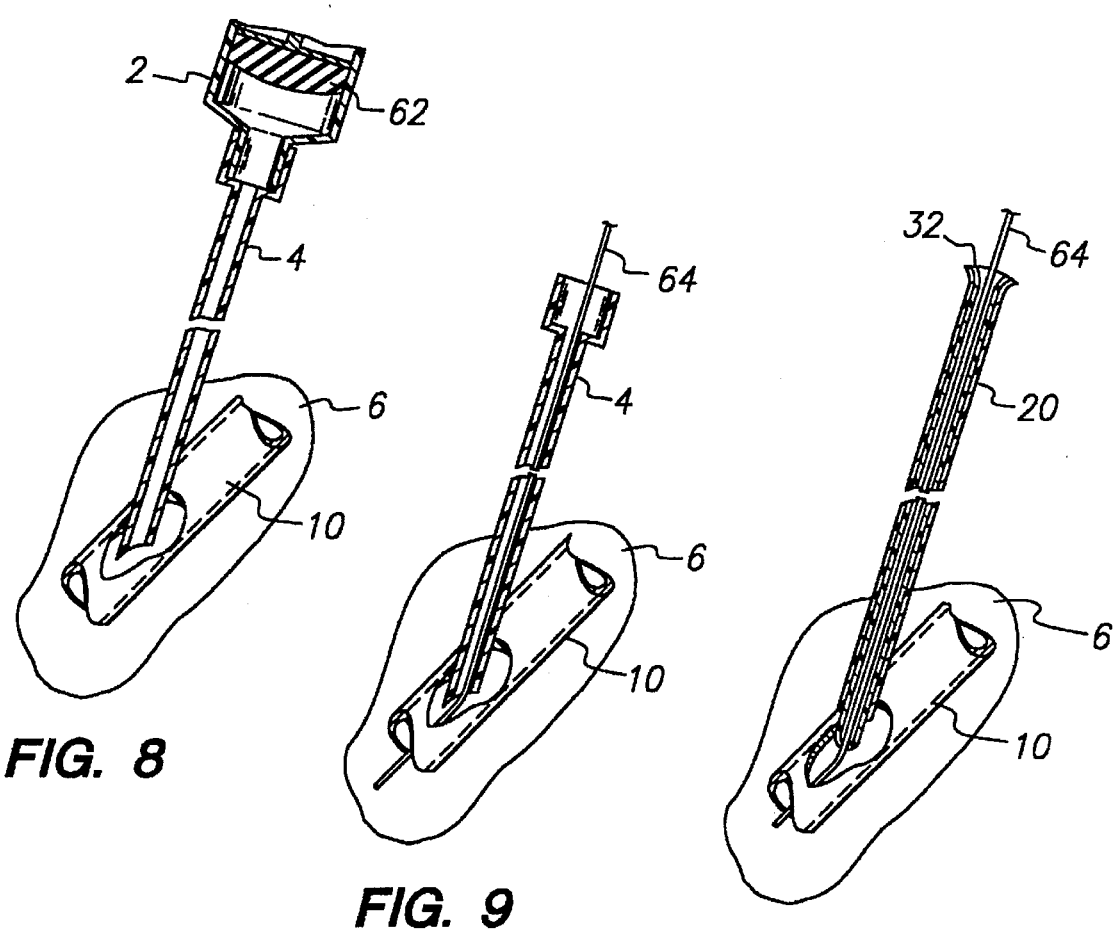
FIG. 8
FIG. 9
FIG. 10

DEVICE FOR USE IN RIGHT VENTRICULAR PLACEMENT AND METHOD FOR USING SAME

BACKGROUND OF THE INVENTION

1. Field of the Invention

The present invention is directed to a device and method especially useful in the insertion of medical devices in the right ventricle of the heart. The invention provides a novel and improved introducer sheath useful in placement of a ventricular pacing lead at the apex of the right ventricle for permanent pacemaker implantation. The present invention also relates to an improved dilator for use with the introducer sheath.

2. Prior Art

Development of permanent implantable pacemaker systems has resulted in life-saving benefits and has greatly improved the quality of life of patients with symptomatic bradyarrhythmias. There are single chamber ventricular pacing methods and dual chamber atrial-ventricular pacing methods. The benefits of dual chamber pacing compared to single chamber ventricular pacing are well documented. Most dual chamber pacing systems use separate atrial and ventricular pacing leads. Permanent pacemaker systems also have been developed which maintain atrial-ventricular synchrony using only a single permanent pacing lead. Such systems are only applicable to specific patient subpopulations. Single chamber atrial pacing is rarely appropriate. Therefore, nearly all patients who undergo permanent pacemaker implantation require ventricular pacing lead placement.

Techniques currently in use for permanent pacemaker implantation typically obtain venous access by one of two methods. A mid infraclavicular incision is made in the skin on either the left or right side of the patient. The left or right subclavian vein is punctured with a thin-walled, large-bore needle and a guidewire is passed into the vein. The needle is removed and an introducer sheath is advanced over the wire with the aid of a dilator into the subclavian vein. After the introducer sheath is in the subclavian vein, the dilator is withdrawn. The pacemaker lead is passed into the venous circulation system through the introducer sheath. The guidewire may be removed or may be left in place as the pacing lead is passed through the system. Current introducer sheaths are only of sufficient length to ensure access to the subclavian vein and, in some patients, to the superior vena cava. Alternatively, a pacemaker lead can be introduced by isolating the cephalic vein and introducing the lead under direct visualization via a venotomy. Regardless of the technique used to obtain venous access, the pacemaker lead must then be advanced via the superior vena cava into the right atrium and then manipulated across the tricuspid valve into the right ventricle and then further advanced past ventricular trabeculae to the apex of the right ventricle for optimal pacing location.

The range of ventricular lead placement devices available for cardiologists and surgeons today are often cumbersome and time consuming to use, especially for cardiologists and surgeons with low annual volumes of pacemaker implantations (i.e. less than 75 pacemaker implants per year). Cardiologists and surgeons frequently have trouble passing the ventricular pacing lead across the tricuspid valve to the apex of the right ventricle because of the interaction of the lead tines or active fixation apparatus with the tricuspid valve or with right ventricle trabeculae. Additionally, the ventricular pacing lead may be inadvertently passed into the coronary sinus. These problems result in increased blood loss and increased radiation exposure for the physician, assistants, and patient.

The present invention is designed to eliminate the problems associated with passing the ventricular pacing lead through the tricuspid valve and past the ventricular trabeculae, prevent inadvertent passing of the pacing lead into the coronary sinus, reduce blood loss, and reduce radiation exposure for the physician, assistants, and patient.

Pacemaker leads are very soft and flexible, thus not easily guided and manipulated into the proper location. Therefore, it is common to use straight and curved stylets to temporarily stiffen the pacing lead and provide directional control to facilitate manipulation of the pacing lead from the right atrium across the tricuspid valve into the right ventricle. Typically, a straight stylet is used to initially introduce the lead into the right atrium. Then the straight stylet is removed and a curved stylet is used to advance the pacing lead across the tricuspid valve into the right ventricle. It is common practice to use the curved stylet to advance the pacing lead past the right ventricle into the right ventricle outflow tract or pulmonary artery to ensure that the pacing lead is not in the coronary sinus. Often times, the curved stylet must be removed and re-shaped during the procedure to attain adequate manipulation and positioning. Then the pacing lead is withdrawn from the right ventricle outflow tract or pulmonary artery using a straight stylet to allow the pacing lead to descend into the apex of the right ventricle for fixation of the pacing lead at the apex with the tines or the active fixation mechanism. Since the coronary sinus does not communicate with the right ventricle outflow tract or pulmonary artery, this technique helps to ensure that the pacing lead is in the right ventricle instead of the coronary sinus. The lead placement procedure is done under fluoroscopy to enable proper pacing lead placement.

The standard method for ventricular pacing lead placement requires extensive lead manipulation, multiple stylet exchanges, and multiple stylet reshapings. In addition, the standard method has potential for inappropriate lead positioning in the coronary sinus and exposing the physician, nurses, and patient to excessive radiation due to the extended use of fluoroscopy.

U.S. Pat. No. 4,243,050 to Littleford discloses a conventional introducer, introducer sleeve and method for implanting pacemaker electrodes in a patient. The introducer and introducer sleeve are dimensioned to only reach into the subclavian vein. Stylets are used inside of the pacing lead in order to advance the lead through the venous system to the apex of the right ventricle.

U.S. Pat. No. 4,467,817 to Harris discloses a small diameter pacing lead of carbon filaments surrounded by a stiffening sheath. The tip of the pacing lead extends beyond the stiffening sheath whereby the stiffening sheath is positioned behind the tip of the pacing lead to assist guiding the pacing lead into the desired organ.

European Patent Application No. 219,608 of Osypka discloses a pacing lead enclosed by a guide sleeve. The guide sleeve is a protective coating that extends over the attaching end of the pacing lead. The guide sleeve has a longitudinal tear line along its length so that it may be separated as it is retracted from the pacing lead.

U.S. Pat. No. 4,602,645 to Barrington et al. discloses a cardiac pacing catheter system used for temporary placement of pacing leads for atrio-ventricular pacing. A standard length introducer sleeve is used to introduce the cardiac pacing catheter system into the subclavian vein. The catheter containing the pacing leads is advanced through the superior vena cava to the entry to the right atrium and then secured in place. Then the ventricular lead is extended into and through the right atrium, through the tricuspid valve and into the right ventricle. Subsequently, the atrial lead is extended into the right atrium.

U.S. Pat. No. 5,246,014 to Williams et al. discloses a complex implantable active fixation lead system consisting of an active fixation pacing lead, an introducer having a coupler which engages a crank portion on the active fixation pacing lead, and a guide catheter that is assembled with the pacing lead and the introducer for imparting stiffness and improved steerability to the pacing lead. The implantable active fixation lead system is inserted through the subclavian vein into the superior vena cava and into the right ventricle through the tricuspid valve. The introducer and active fixation pacing lead are extended past the guide catheter in the area of the right ventricle apex. The active fixation pacing lead is then cranked into the cardiac tissue by rotating the introducer.

In view of the limitations and complexities of the prior art devices, it would be highly desirable to have an apparatus and method that would facilitate simple, rapid permanent pacemaker ventricular pacing lead placement requiring little or no lead manipulation, eliminate the need for multiple stylets, and decrease the risk of inappropriate lead placement.

SUMMARY OF THE INVENTION

One object of the subject invention is to make permanent pacemaker ventricular pacing lead placement a simple, rapid procedure requiring little or no lead manipulation, eliminate the need for multiple stylets, and decrease the risk of inappropriate lead placement in the coronary sinus while maintaining (or increasing) the safety and rapidity of the procedure.

To accomplish this purpose there is provided an introducer sheath that is of sufficient length to reach from an incision over the cephalic vein on either the right or left side of the patient to the apex of the right ventricle. The introducer sheath can be passed through the tricuspid valve to the apex of the right ventricle over a guidewire or a balloon-tipped catheter. The introducer sheath acts as a guide passage for a pacing lead, a guidewire, a balloon-tipped catheter, etc. The ventricular apex at the lowermost portion of the right ventricle is concave and provides a stable location in which the pacemaker lead will not become dislodged as the heart flexes and pumps repeatedly. The introducer sheath acts as a guide chute for the ventricular lead to prevent interaction of the lead tines with either the tricuspid valve or the right ventricle trabeculae. When the pacemaker lead has been positioned at the apex of the right ventricle, the introducer sheath is removed using peel-away or slitting techniques.

In one aspect of the invention there is provided a device for use in rapid, atraumatic placement of medical devices in a right ventricle of a patient comprising: an introducer sheath used as a passage for intravenous placement of a medical device in a patient's heart, the introducer sheath being of sufficient length to allow a proximal end thereof to be located outwardly from an incision in the skin of the patient over the cephalic vein when a distal end of said introducer sheath is at an apex of the right ventricle, being of sufficient flexibility to pass through a tricuspid valve, and being of sufficient strength to allow the introducer sheath to be pushed along the length thereof through a tortuous path from the mid infraclavicular puncture to the apex of the right ventricle; said introducer sheath having an inside diameter of sufficient size to slidably receive a balloon-tipped catheter therein.

In another aspect of the invention there is provided a device for use in rapid, atraumatic placement of medical devices in a right ventricle of a patient comprising: an introducer sheath used as a passage for intravenous placement of a medical device in a patient's heart, said introducer sheath being of sufficient length to allow a proximal end thereof to be located outwardly from an incision in the skin of the patient over the cephalic vein when a distal end of said introducer sheath is at an apex of the right ventricle, being of sufficient flexibility to pass through a tricuspid valve, and being of sufficient strength to allow the introducer sheath to be pushed along the length thereof through a tortuous path from the mid infraclavicular puncture to the apex of the right ventricle; said introducer sheath having a tapered distal segment and an inside diameter of sufficient size to pass a removable flexible guidewire or pacing lead therethrough.

In yet another aspect of the invention there is provided a kit for rapid, atraumatic right ventricular placement of medical devices comprising: a guide member; an introducer sheath used as a passage for intravenous placement of a medical device in a patient's heart, said introducer sheath being of sufficient length to allow a proximal end thereof to be located outwardly from an incision in the skin of the patient over the cephalic vein when a distal end is at an apex of the right ventricle, being of sufficient flexibility to pass through a tricuspid valve, being of sufficient strength to allow the introducer sheath to be pushed along the length thereof through a tortuous path from the mid infraclavicular puncture to the apex of the right ventricle, and having an inside diameter of sufficient size to pass said guide member therethrough; a dilator having a taper at a distal end, a central bore of sufficient size for passing the guide member therethrough, an outside diameter configured for a close fit of said dilator in said introducer sheath, and having a length greater than the length of the introducer sheath.

In one of its method aspects there is provided a method for rapid, atraumatic right ventricular placement of medical devices across a tricuspid valve to an apex of a right ventricle in the heart of a patient comprising: providing a guide member and a hollow needle having an inside diameter sufficient to pass said guide member; providing an introducer sheath used for intravenous placement of a medical device in a patient's heart, said introducer sheath being of sufficient length to allow a proximal end thereof to be located outwardly from an incision in the skin of the patient over the cephalic vein when a distal end is at an apex of the right ventricle, being of sufficient flexibility to pass through a tricuspid valve, being of sufficient strength to allow the introducer sheath to be pushed along the length thereof through a tortuous path from the mid infraclavicular puncture to the apex of the right ventricle, and having an inside diameter of sufficient size to pass said guide member; making an incision in the skin of the patient; inserting said needle into a vein of the patient; passing said guide member through said needle into the subclavian vein and into a superior vena cava; removing said needle; advancing said guide member across the tricuspid valve to the apex of the right ventricle; and advancing the introducer sheath over said guide member across the tricuspid valve into the vicinity of the apex of the right ventricle.

DESCRIPTION OF THE DRAWING

FIG. 1 is a plan view of a patient with a needle being inserted through the subclavian vein to communicate with the heart of the patient.

FIG. 2 is a plan view of a patient with a completed implant of a pacemaker set.

FIG. 3 is a perspective view of an introducer sheath used to implant a pacing electrode in the patient.

FIG. 3A is a perspective view of an alternate embodiment of the introducer sheath of FIG. 3.

FIG. 7 is a perspective view of a balloon-tipped catheter for use with the present invention.

FIG. 8 is a perspective view of a needle puncturing the subclavian vein in accordance with a method of the present invention.

FIG. 9 is a perspective view of a guidewire being introduced through the needle into the subclavian vein.

FIG. 10 is a perspective view of the dilator and introducer sheath of FIGS. 3 and 3A being inserted over the guidewire into the subclavian vein.

DESCRIPTION OF THE PREFERRED EMBODIMENTS

Figure 4:
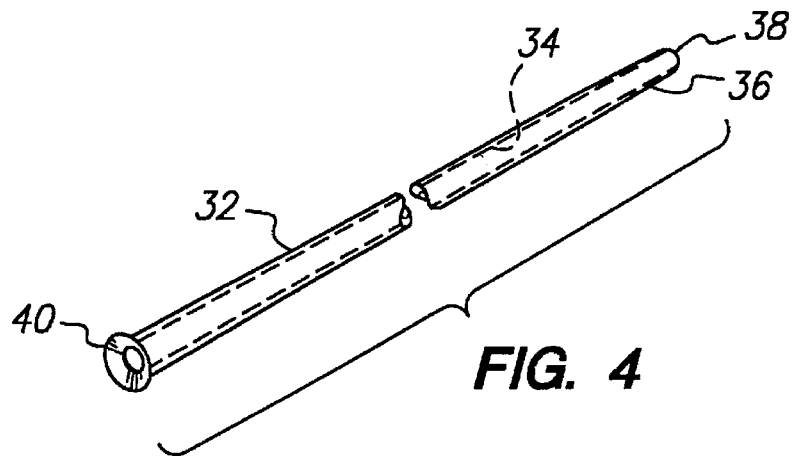
FIG. 4 is a perspective view of one embodiment of a dilator in accordance with the present invention.

With continued reference to the drawing, FIG. 1 illustrates a syringe 2 with a needle 4 being inserted in the patient 8 to obtain access to the subclavian vein 10. The subclavian vein 10 is a large vein and readily receives a permanent pacemaker pacing lead. The insertion of the needle 4 is the first step in the method of implanting a pacemaker electrode with minimal incision to the patient. Typically the needle 4 is inserted at a mid infraclavicular position made on the right side of the patient's chest to obtain access to the right subclavian vein. However, the insertion can be made on the left side of the patient's chest to obtain access to the left subclavian vein. As shown in FIG. 2, the patient 8 has a pacing lead 12 extending through the subclavian vein 10 to the heart 14. A pacemaker set 16 is shown implanted within the patient 8.

Access to the subclavian vein 10 can also be attained by sectioning through the tissue layers of the patient 8 down to the cephalic vein 9. The cephalic vein 9 is located in the deltopectoral groove of the chest wall. The cephalic vein 9 extends beneath the clavicle, running ultimately to the subclavian vein 10. After sectioning through the tissue layers to isolate the cephalic vein 9, an incision is made in the cephalic vein 9 and the pacing lead 12 is inserted through the incision and advanced through the cephalic vein 9 to the subclavian vein 10 and then into the heart 14.

One embodiment of an introducer sheath 20 in accordance with the present invention is shown in FIG. 3. The introducer sheath 20 can be used in either of the methods just described and in a method of inserting the pacing lead 12 into the patient 8 as described later. The introducer sheath 20 has an inside diameter 22, a tapered distal segment 24, and a flared proximal end 26. The distal segment 24 and the proximal end 26 can be straight.

The introducer sheath 20 has sufficient flexibility to pass from an incision in the exterior skin 6 over the cephalic vein 9 of patient 8 through the tortuous path in the venous system to the apex AP of the right ventricle of the patient's heart 14. As will be described in more detail below. The introducer sheath 20 is of sufficient length to reach the apex AP of the right ventricle but, in accordance with safe medical practice, during use the distal end is not advanced into contact with the apex AP of the right ventricle instead the distal end is positioned at a location in the vicinity of the apex AP of the right ventricle so as to prevent damage to or perforation of the heart. Particularly, the introducer sheath 20 is of sufficient flexibility to pass through the tricuspid valve of the heart 14 and the narrow passage between the clavicle and first rib. However, the introducer sheath 20 has sufficient strength to allow it to be pushed along its length thereof through that tortuous path. To achieve the necessary combination of flexibility and strength, particularly at the level of the clavicle and first rib where there is minimal clearance, the introducer sheath is of varied stiffness, being more flexible towards distal end 25 and is more stiff towards proximal end 26. For example, this variation in stiffness can be provided in an introducer sheath wherein the wall thickness or the diameter of the introducer sheath 20 can decrease from the proximal end 26 to the distal end 25 while maintaining a constant inside diameter to effect a gradual transition from proximal stiffness to distal flexibility. The variation in stiffness can be along the entire length of the introducer sheath 20 or along a portion of the length. The transition in stiffness can be gradual or can be incremental in multiple stages or sections. There can be two, three, or more sections with decreasing stiffness. Preferably, the distal end 25 is soft and flexible so as to be atraumatic. Particularly, the portion that extends from the superior vena cava SVC to the apex AP of the right ventricle RV is soft and flexible. The variation in stiffness along the relevant portion of the introducer sheath can be achieved by varying the wall thickness, varying the material, such as a polymer of varying density and stiffness (thus enabling constant wall thickness), varying a polymer or metal composition mixture, imparting varied-properties, such as a varied degree of cross-linking (chemical, radiation, etc.) of a polymer, or by a variety of other means which will be apparent to one of ordinary skill in the art following the teachings herein.

The introducer sheath 20 can be relatively flexible because during the majority of its use it is supported internally by a dilator, guide member, balloon-tipped catheter, pacing lead, etc. If the introducer sheath 20 collapses or kinks during use one of the identified components can be inserted through the introducer sheath 20 to straighten it. Preferably, the introducer sheath 20 is sufficiently flexible or soft at the distal end 25 to prevent inadvertent perforation of the myocardium. The introducer sheath can be made of any suitable material having desired strength, flexibility and/or biocompatability properties. Preferably, the introducer sheath 20 has a low-friction surface such as a polymeric material, a photopolyacrylamide-heparin complex, a polyethylene glycol, a hyaluronic acid, or a polyvinylpyrrolidone material (all available from Biometric Systems, Inc., Minneapolis, Minn.).

The inside diameter 22 of the introducer sheath is of sufficient size to slidably receive a number of components, such as dilators, guide members, balloon-tipped catheters, pacing leads, or the like. The introducer sheath acts as a guide passage for these components. Preferably, the inside diameter 22 has a low-friction surface so as to allow the components to pass easily through the introducer sheath. As will be recognized by one of ordinary skill in the art, many polymeric materials and coatings, such as fluorocarbons, will provide the desired lubricousness as well as the surfaces discussed above. The inside diameter 22 typically is constant along the length of the introducer sheath and will range from 2 French (2F) to 14 French (0.66 mm to 3.96 mm) depending on the diameter of the components in use therewith. The wall thickness will typically range from 0.17 mm to 0.25 mm. However, smaller and larger sizes can be used should smaller or larger devices need to be introduced into the right ventricle.

Introducer sheath 20 in accordance with the present invention is of greater length than sheaths previously used for right ventricular placement of pacing leads. Introducer sheath 20 is of sufficient length to allow proximal end 26 to be located outwardly from either a right side or left side incision in the exterior skin 6 of the patient 8 over the cephalic vein 9 when distal end 25 is at the apex AP of the right ventricle in the patient's heart 14. Typically, the length of the introducer sheath will range from 20 cm to 75 cm depending on the size of the patient, the length of the pacing lead, etc. Preferably, the introducer sheath is 40 to 60 cm long.

The introducer sheath 20 can also comprise a plurality of perforations 28 to form a weakened line along the length of the introducer sheath 20 to allow the introducer sheath to be split apart or peeled away in order to remove it from the patient 8. Preferably, the perforations are indentations which do not extend completely through the thickness of the introducer sheath 20 so that air does not flow through them.

In another embodiment of the introducer sheath 20 shown in FIG. 3A, a groove 30 forms the weakened line along the length of the introducer sheath 20. The plurality of perforations 28, groove 30, or other weakening means can be in one or more locations around the circumference of the introducer sheath 20 for enabling the introducer sheath 20 to be severable along the length thereof. The weakening means can take a number of forms such as reduced wall thickness or integral cutting agents such as strings and the like.

Figure 17:
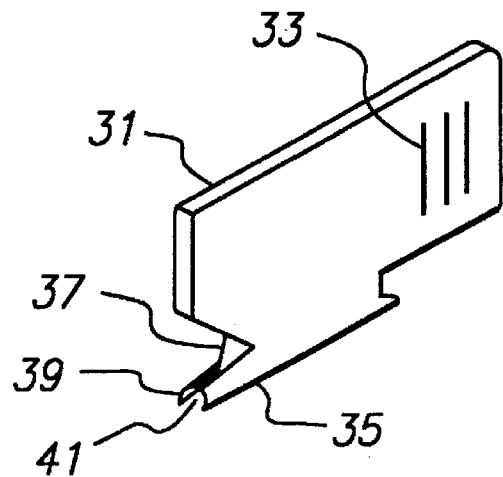
FIG. 17 is a perspective view of a slitter for use with the present invention.

As an alternative to or in addition to the groove or plurality of perforations, a slitter 31 shown in FIG. 17 can be used to cut apart the introducer sheath 20. The slitter 31 has a gripping area 33 for holding and guiding the slitter when in use. A frusto-conical portion 35 leads to a blade 37 that is used to split apart the introducer sheath 20. The method of using the slitter, groove, plurality of perforations, or other weakening means will be discussed later.

FIG. 4 is one embodiment of a dilator 32 in accordance with the present invention. The dilator 32 has an inside diameter 34, a taper 36 at a distal end 38, and a flared proximal end 40. The dilator 32 is configured to have an outer diameter that closely fits the inside diameter 22 of introducer sheath 20 when the flared proximal end 40 abuts flared proximal end 26 and the taper 36 extends beyond the tapered distal segment 24 of introducer sheath 20. That is, the outer diameter of the dilator 32 is slightly smaller than the inside diameter of the introducer sheath 20 so that the dilator 32 can slide into the introducer sheath 20 without undue friction between the introducer sheath 20 and the dilator 32. The inside diameter 34 is sufficient for the dilator 32 to pass over a guide member, such as a flexible guidewire having a diameter of 0.66 mm to 0.99 mm. The guidewire can be any conventionally used guidewire.

In another embodiment, the outside diameter of the introducer sheath 20 can be tapered from the proximal end 26 to the distal end 25 or the introducer sheath can have an increasing wall thickness from the distal end 25 to the proximal end 26 to provide greater flexibility along its length near the distal end 25 and greater strength along its length near the proximal end 26. Likewise, the introducer sheath 20 can comprise several sections of varying stiffness, the material can be cross-linked, etc. In yet another embodiment, the outside diameter of the dilator 32 can be tapered from the proximal end 40 to the distal end 38 to closely fit the inside diameter of the introducer sheath 20. The introducer sheath 20 preferably only has increased flexibility along the distal portion extending from the superior vena cava SVC to the apex AP of the right ventricle RV.

Figure 5:
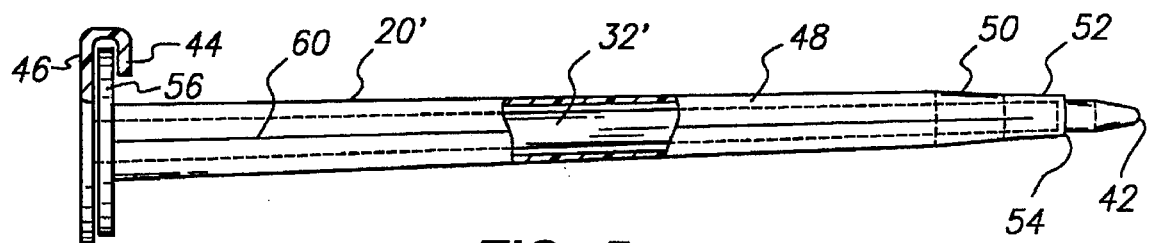
FIG. 5 is a plan view of another embodiment of a dilator inserted in an introducer sheath in accordance with the present invention.
Figure 5A:
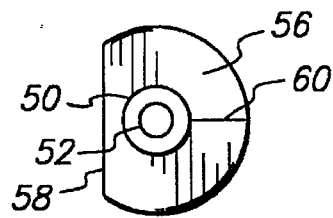
FIG. 5A is an end view of the proximal end of the introducer sheath of FIG. 5.

FIGS. 5 and 5A illustrate an alternate embodiment of the dilator and introducer sheath. The dilator 32' has a tapered distal end 42 and a central bore (not shown) configured to receive a guide member. The dilator 32' has a clip 44 attached to the proximal end 46, the clip extending in the distal direction and then radially inwardly. The introducer sheath 20' has a first portion 48 having an inside diameter greater than the outside diameter of the dilator 32'. The introducer sheath 20' can be slightly tapered from the distal end of the first portion 48 along tapered segment 50 to a cylindrical portion 52. In the alternative, the introducer sheath 20' can be tapered from the distal end of the first portion 48 all the way to distal end 54. Preferably, the distal end 54 of the introducer sheath 20' is rounded to prevent damage during entry into the subclavian vein 10.

The introducer sheath 20' further includes a flange 56 at its proximal end. The flange 56 can have a flat portion 58 (FIG. 5A) along its periphery corresponding to the shape and size of the clip 44 of the dilator 32'. The clip 44 and flange 56 can be locked together by axially sliding the introducer sheath 20' onto the dilator 32' so that the flat portion 58 passes under the clip 44 and then by rotating the introducer sheath 20' so that flange 56 engages clip 44. This allows the introducer sheath 20' to be detachably mated with the dilator 32' to prevent separation of the introducer sheath and dilator during insertion and manipulation of the two in the patient's body. The introducer sheath 20' can further include a groove or slit 60 extending through the flange 56 along the first portion 48 into the taper 50. The groove or slit 60 through the flange 56 allows the flange 56 to be broken apart so that the introducer sheath 20' can be pulled apart along the groove 60. Preferably, the introducer sheath 20' and dilator 32' are made of a polypropylene material.

FIGS. 8–16 illustrate the methods of inserting the pacing lead 12 into the patient's heart 14. The heart 14 and associated structures include the subclavian vein 10, superior vena cava SVC, inferior vena cava IVC, right atrium RA, tricuspid valve TCV, right ventricle RV, apex AP of the right ventricle, pulmonary artery PA, left ventricle LV, mitral valve MV, left atrium LA, and aorta A.

Figure 6:
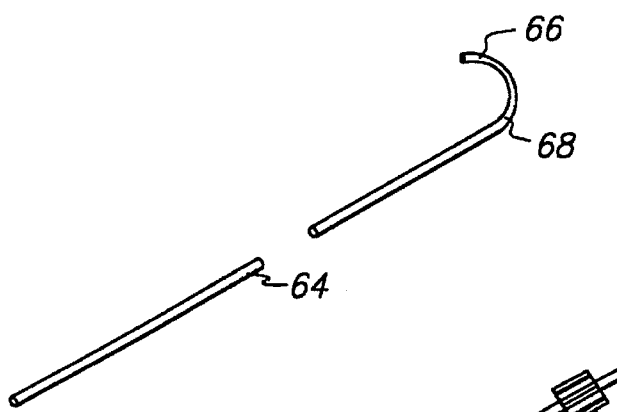
FIG. 6 is a perspective view of a flexible guidewire for use with the present invention.
Figure 6A:
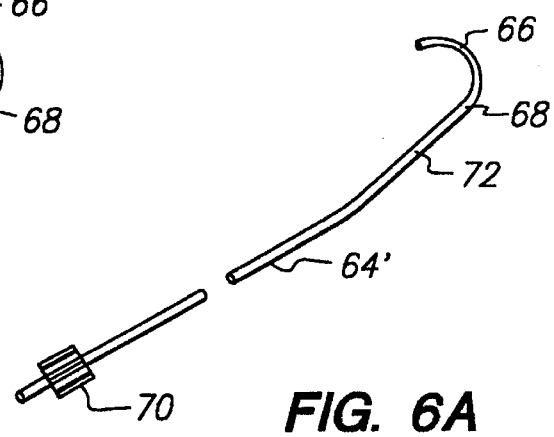
FIG. 6A is a perspective view of an alternate embodiment of the flexible guidewire of FIG. 6.

FIG. 8 shows the needle 4 puncturing the exterior skin 6 of the patient 8 to enter the subclavian vein 10. Preferably, an 18 gauge, thin wall needle is employed in accordance with the present invention. However, the size of the needle can be smaller or larger depending on the size of the components to be used therewith such as a guidewire, etc. A piston 62 of syringe 2 is withdrawn slightly to draw a small quantity of blood from the subclavian vein 10 to insure that the needle 4 has entered the vein. The syringe 2 is removed from the needle 4. A flexible guide member 64 as illustrated in FIG. 6 or 6A is pushed through the needle 4 to enter the subclavian vein 10 as shown in FIG. 9. Alternatively, the flexible guide member 64 can be advanced into the subclavian vein 10 through the cephalic vein as discussed above.

The flexible guide member 64 can be a straight, J-tipped guidewire as shown in FIG. 6. The guide member 64 is of sufficient diameter to pass through the needle 4. Typically, guidewire diameters range from 2F to 3F (0.66 mm to 0.99 mm). The guide member 64 preferably has a flexible J-tip 66 at a distal end 68. The curved segment extends through an arc of approximately 150° and typically has a radius of 3.0 to 6.0 mm. The J-tip is flexible so that it will flex easily to a straight configuration so as to be easily slidable through the needle 4. However, the curved segment is resiliently biased so that when it exits the needle it assumes its J-shape in a relaxed state. The guide member 64 typically will range in length from 40 cm to 120 cm, but preferably is 100 cm long.

Figure 11:
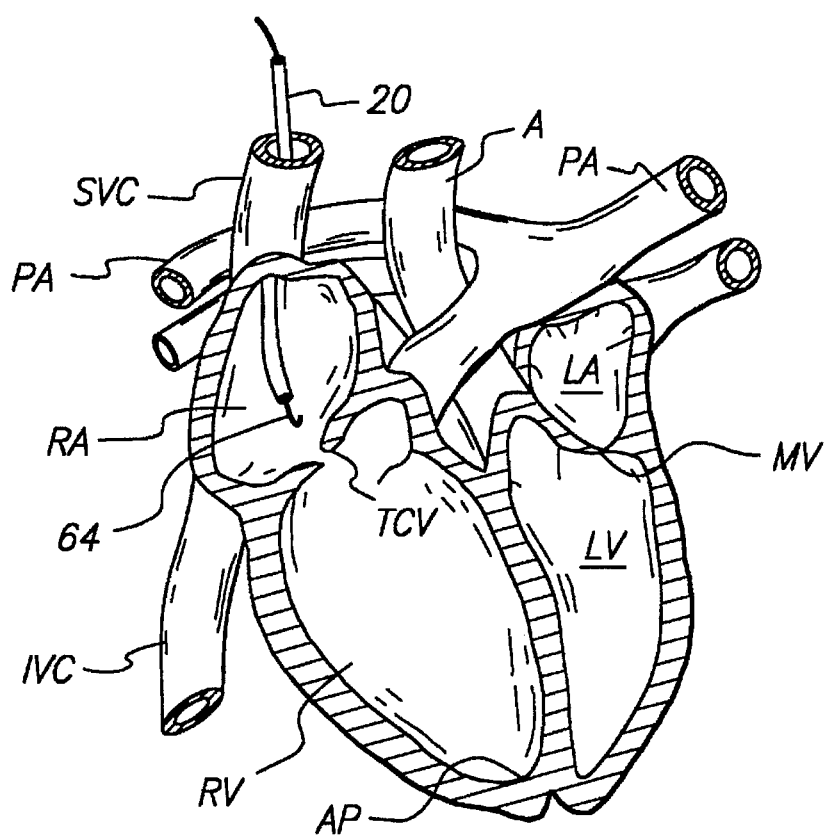
FIGS. 11–16 illustrate diagrammatically portions of a patient's heart and the manner in which the present invention is used.

FIG. 6A illustrates an alternative configuration for the guide member. Guide member 64' is an angled, J-tipped guidewire with an angled segment 72. Preferably, the angulation of the guidewire is approximately 135° and occurs at about 4 cm from the J-tip 66 at the distal end 68. A removable torquing or steering device 70 can be attached to guide member 64'. The steering device 70 facilitates rotation of the guide member 64' to orient the angled segment directionally toward the tricuspid valve TCV (FIG. 11).

Figure 6B:
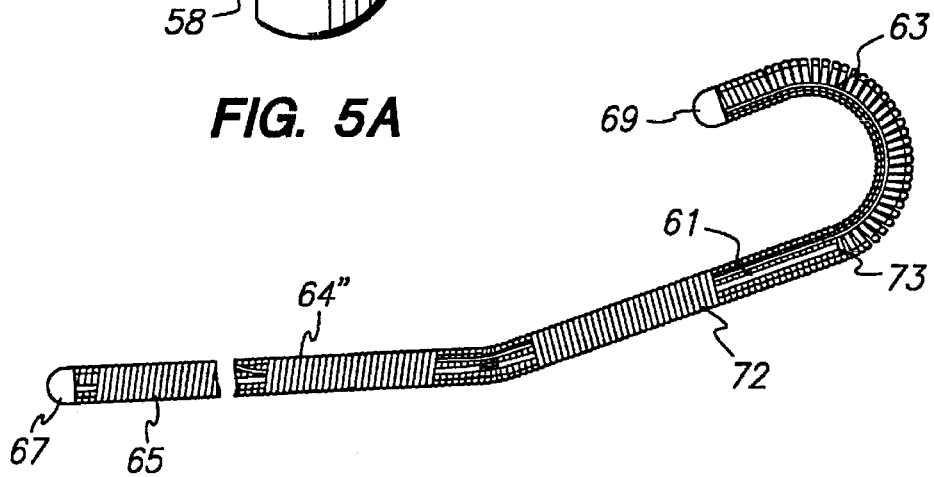
FIG. 6B is a plan view of an alternate embodiment of the flexible guidewire of FIG. 6.

FIG. 6B illustrates another embodiment for the guide member. The guide member 64" is comprised of three wires. An outer coiled wire 65 extending from proximal end 67 to distal end 69. The wire diameter is typically 0.178 mm and is coiled to form an overall coil diameter ranging from 2F to 3F (0.66 mm to 0.99 mm). The outer coiled wire 65 can be stainless steel, coated with tetrafluoroethylene fluorocarbon polymers such as the one sold under the trade name "TEFLON" (available from E.I. DuPont de Nemours Co., Wilmington, Del., 19898) and/or heparin bonded. Within the coiled wire 65, there is a holding wire 63 attached to the distal end 69 and at a point near the proximal end 67 to minimize the possibility of coil fracture or stretching. The holding wire diameter typically ranges from 0.30 mm to 0.51 mm. Also within the coiled wire 65 is a support wire 61. The desired angled segment 72 can be formed by angling the support wire 61. In addition, the support wire 61 can be a flat, formable wire (i.e., ribbon-type wire 0.254 mm wide and 0.076 mm thick) to help facilitate angulation.

The support wire 61 can be either fixed or movable. The fixed support wire extends from the proximal end 67 to a point 73 at the beginning of the flexible J-tip 66. The fixed support wire typically tapers over its distal-most portion (i.e., approximately the last 6 cm. If the support wire 61 is movable, the location of the angulation is movable as well to accommodate variously shaped hearts. The movable support wire can be coated with tetrafluoroethylene fluorocarbon polymers such as the one sold under the trade name "TEFLON" (available from E.I. DuPont de Nemours Co., Wilmington, Del., 19898) to provide free movement within the outer coiled wire 65. The support wire 61 and holding wire 63 can be stainless steel, coated with tetrafluoroethylene fluorocarbon polymers such as the one sold under the trade name "TEFLON" (available from E.I. DuPont de Nemours Co., Wilmington, Del., 19898), and/or heparin bonded.

The needle 4 is then removed enabling the dilator 32 and introducer sheath 20 to be guided over the guide member 64 to enter the subclavian vein 10 as shown in FIG. 10. The dilator 32 adds mechanical strength to the introducer sheath 20 during entry into the patient 8 through soft tissue and muscle until the dilator 32 and introducer sheath 20 reach the venous system. The dilator 32 is removed after the introducer sheath is sufficiently inserted into the superior vena cava SVC over guide member 64. The dilator 32 and introducer sheath 20 can be guided over the guide member 64 whether the guide member 64 is inserted in the cephalic vein or the subclavian vein.

Typical introducer sheaths are only long enough to be advanced into the superior vena cava SVC. However, the introducer sheath of the present invention can be advanced past the superior vena cava SVC. FIG. 11 shows the introducer sheath 20 advanced over the guide member 64 into the right atrium RA. Preferably, the introducer sheath 20 is advanced through the superior vena cava SVC into the right atrium RA under fluoroscopy.

Figure 12:
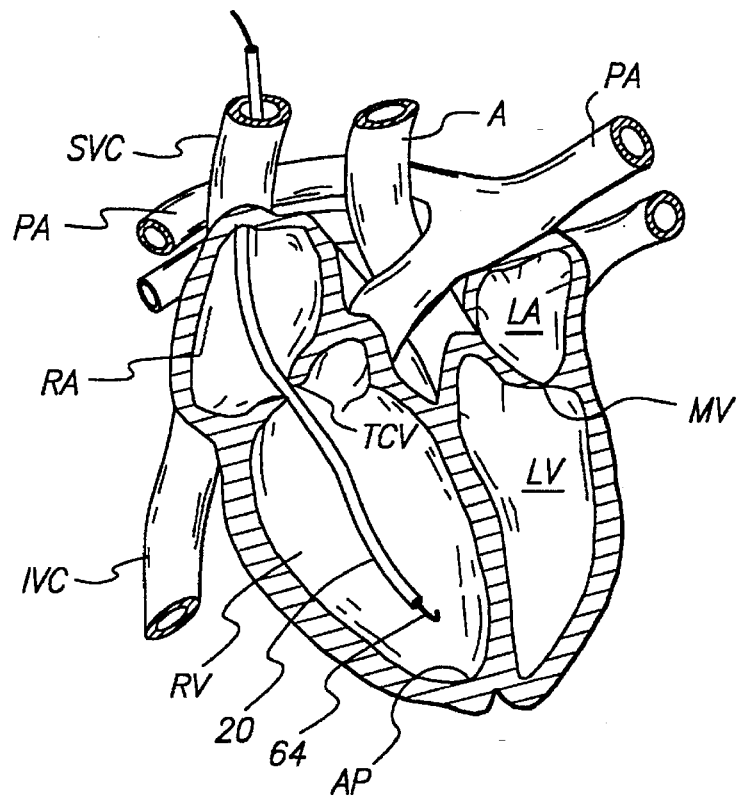

In many cases, the straight, J-tipped guidewire 64 or angled, J-tipped guidewire 64' can be advanced into the right ventricle RV. The preformed, J-shaped curve on the distal end of the guide member facilitates crossing the tricuspid valve TCV atraumatically. If the guide member 64 or 64' passes easily into the right ventricle RV through the tricuspid valve TCV, the introducer sheath 20 can be advanced over the guide member 64 or 64' into the right ventricle RV as shown in FIG. 12. The introducer sheath 20 is advanced over the guide member 64 or 64' by pushing along the length of the introducer sheath that is located outwardly from the mid infraclavicular puncture in the patient's skin. Once the introducer sheath 20 is positioned in the right ventricle RV in the vicinity of the apex AP, the guide member 64 or 64' can be withdrawn. If preferred, the guide member 64 or 64' can be retained.

If the guide member 64 or 64' does not pass easily through the tricuspid valve TCV, the guide member 64 or 64' is removed and a balloon-tipped, flotation catheter 64A as shown in FIG. 7 is inserted in the introducer sheath 20. The balloon-tipped catheter 64A is typically 40 cm to 95 cm in length and preferably 75 cm. The outside diameter of the balloon-tipped catheter typically ranges from 4F to 8F (1.32 mm to 2.64 mm) and preferably is 5F (1.65 mm).

Figure 12A:
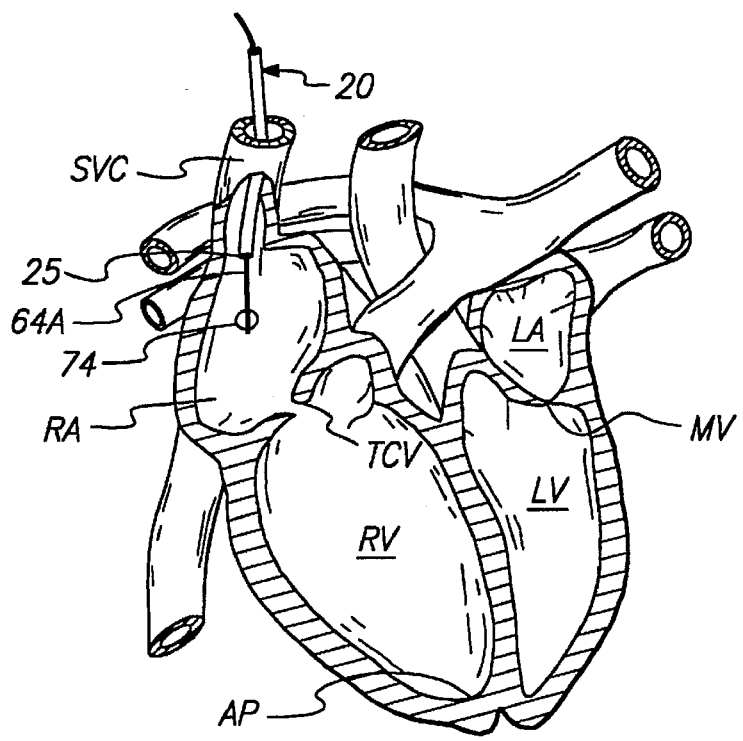

The balloon-tipped catheter 64A is advanced in a deflated position through the introducer sheath 20 until it exits the distal end 25 of the introducer sheath 20 in the right atrium RA as shown in FIG. 12A. The balloon 74 is inflated after it exits the distal end 25 of the introducer sheath 20 by opening the stop cock 75 of valve 76 attached to the proximal end 78 of the balloon-tipped catheter 64A (FIG. 7) and depressing the piston 80 of syringe 82 which is attached to valve 76. The piston 80 forces air in the syringe 82 through an inflation lumen in the balloon-tipped catheter 64A and into the balloon 74 through opening 84. After inflating the balloon 74, the stop cock 75 is closed so that the balloon 74 remains inflated. The inflated balloon diameter is approximately 1 cm. It will be appreciated by one of ordinary skill in the art that other balloon-tipped catheters commonly known in the art such as double or triple lumen balloon-tipped catheters can be used in accordance with the present invention.

Figure 13:
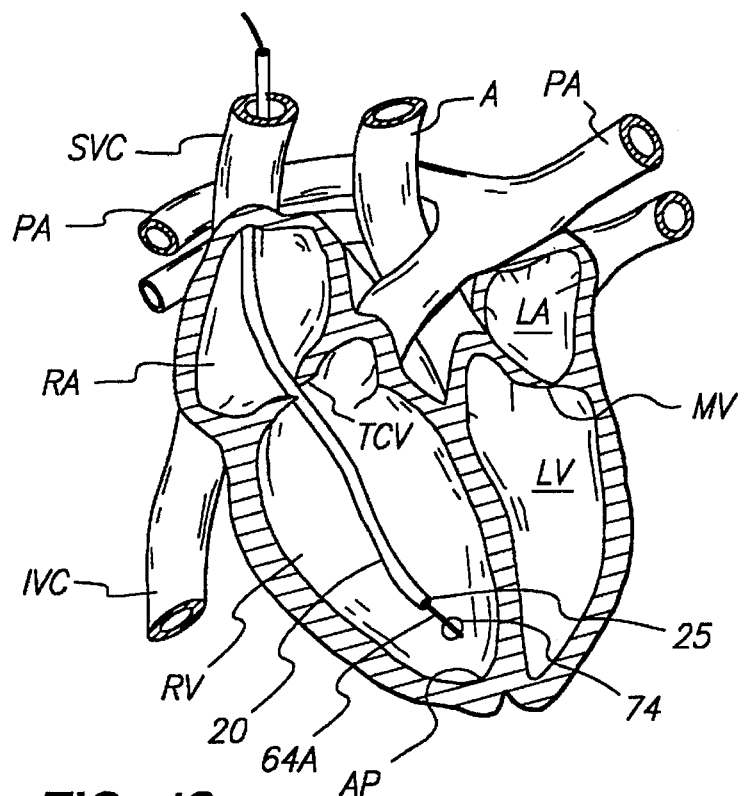

The introducer sheath 20 is stabilized with its distal end 25 in the right atrium RA and the balloon-tipped catheter 64A is advanced under fluoroscopy through the tricuspid valve TCV taking advantage of the flow-directed properties of the inflated balloon 74 to be carried by the blood flow into the right ventricle RV instead of into the inferior vena cava IVC. The balloon-tipped catheter 64A is advanced to the vicinity of the apex AP of the right ventricle RV. The position of the balloon-tipped catheter 64A can be confirmed fluoroscopically. After stabilizing the position of the balloon-tipped catheter 64A, the introducer sheath 20 is advanced across the tricuspid valve TCV over the balloon-tipped catheter 64A until its distal end 25 is close to or meets the inflated balloon 74 as shown in FIG. 13. Preferably, the balloon 74 is left inflated to prevent advancing the introducer sheath 20 too far and possibly perforating the apical myocardium of the right ventricle RV.

A radio-opaque distal tip marker such as barium sulphate on the introducer sheath 20 can be provided to improve fluoroscopic visualization of the distal end 25 of the introducer sheath 20. Likewise, other radio-opaque markers can be used, or a portion of or the entire length of the introducer sheath can be radio-opaque. In addition, the balloon-tipped catheter 64A can have similar types of radio-opaque markers. Radio-opaque markers along the introducer sheath 20 can be used to measure the proper length of a permanent pacemaker pacing lead. In this way, a pacing lead that is too short or too long won't first be inserted and then have to be removed and replaced with a proper length lead as sometimes occurs with conventional methods.

Figure 14:
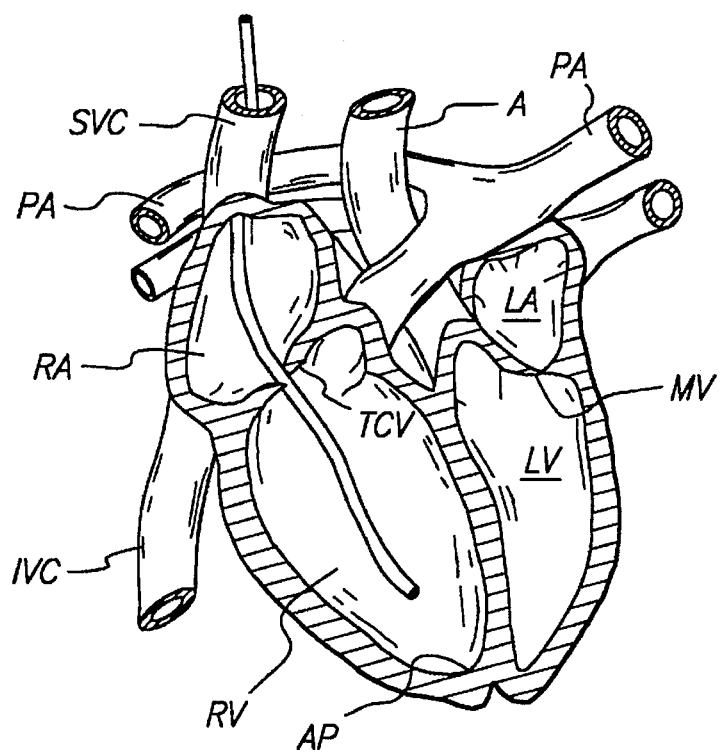
Figure 15:
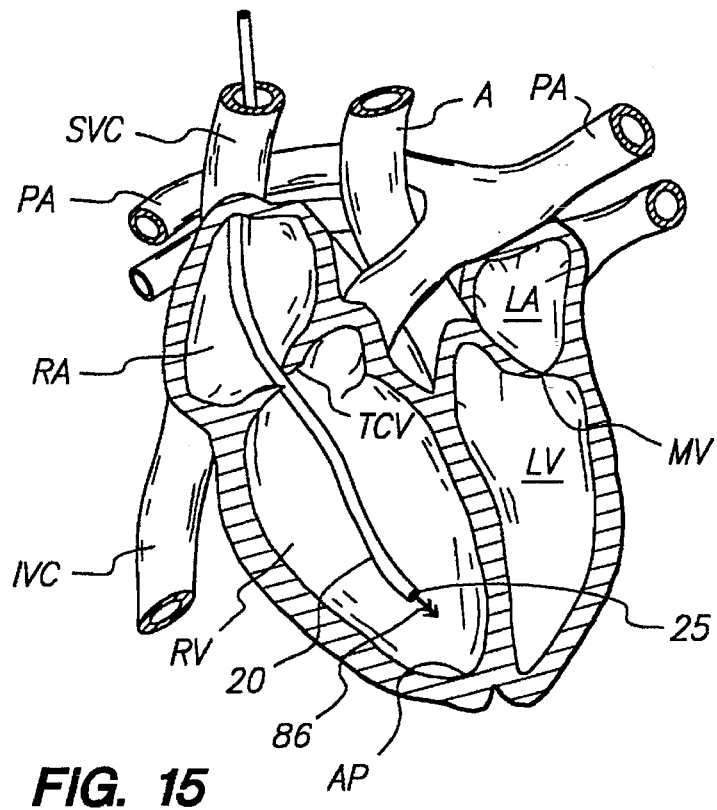

After stabilizing the introducer sheath 20 in position in the vicinity of the apex AP of the right ventricle RV, the balloon 74 is deflated by opening stop cock 75 and the balloon-tipped catheter 64A is withdrawn and removed from the patient 8 as seen in FIG. 14. After completely removing the balloon-tipped catheter 64A, a permanent ventricular pacing lead 86 is advanced through the introducer sheath 20 directly into the right ventricle RV without the possibility of inadvertently passing into the coronary sinus or becoming entangled in the tricuspid valve TCV or with right ventricle trabeculae (FIG. 15). With the introducer sheath 20 of the present invention advanced through the tricuspid valve TCV, there is no need to use a curved stylet to advance the pacing lead 86 into the right ventricle RV as is usually necessary with conventional introducer sheaths. A straight stylet in the pacing lead 86 is sufficient. The pacing lead 86 can also have sufficient strength itself to pass through the introducer sheath 20 into the right ventricle RV without the need for any stylet.

It is not necessary, and may not be desirable, for the pacing lead 86 to exit from the distal end 25 of the introducer sheath 20. Advancing the pacing lead 86 out the distal end 25 of the introducer sheath 20 increases the risk of perforating the apex AP of the right ventricle RV. Likewise, manipulating the introducer sheath 20 in a forward direction in the vicinity of the apex AP of the right ventricle RV should not be done as damage to the introducer sheath 20 or trauma to the right ventricle RV may occur. The radio-opaque markers could serve to identify how far in a distal direction to advance the pacing lead 86. In addition, if re-positioning of the introducer sheath 20 is desired, the balloon-tipped catheter 64A can be reinserted and advanced to the apex AP of the right ventricle RV so that the introducer sheath 20 can be advanced over the body of the balloon-tipped catheter 64A.

Figure 16:
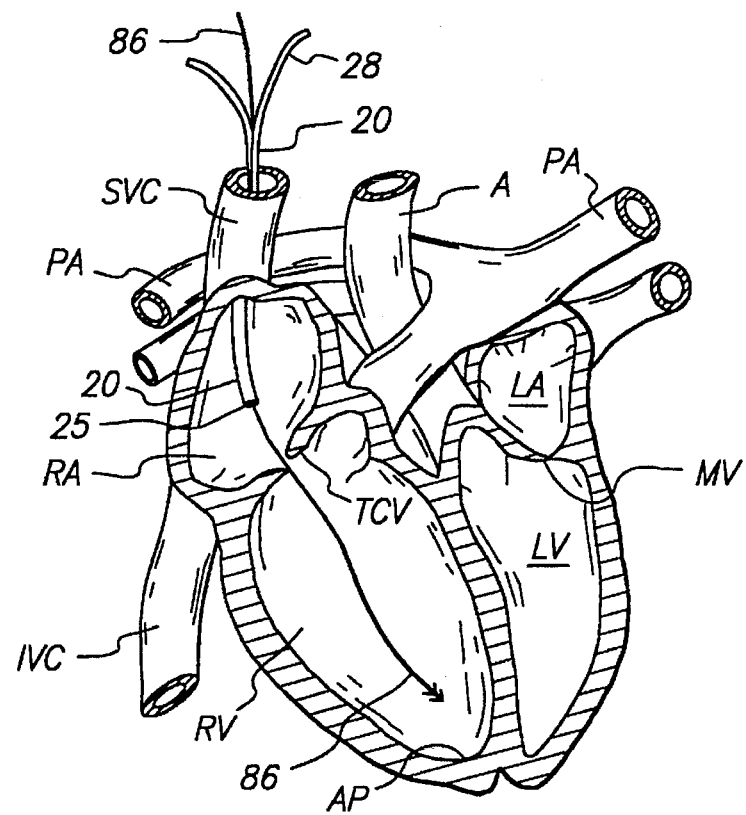

When the pacing lead 86 has been positioned near the apex AP of the right ventricle so as to achieve adequate pacing and sensing, the introducer sheath 20 is withdrawn and removed from the patient 8. The introducer sheath 20 is withdrawn and removed from the pacing lead 86 by sliding the introducer sheath 20 proximally over the pacing lead 86 and splitting apart the introducer sheath 20 along the plurality of perforations 28, groove 30, or whatever weakening means exists as shown in FIG. 16.

Because of the length of the introducer sheath 20 and the need for the position of the pacing lead 86 to remain stable, optimal introducer sheath 20 removal may require a scalpel-like, slitter 31 as shown in FIG. 17 and described above. Channel 41 of frusto-conical portion 35 can be attached to the body of the pacing lead 86 to facilitate slitting of the introducer sheath 20 during withdrawal of the introducer sheath 20. The frustum 39 is inserted into the introducer sheath 20 and the introducer sheath 20 is pulled proximally over the frusto-conical portion 35 to engage the scalpel-like blade 37. The blade 37 cuts the introducer sheath 20 and the conical shape of the frusto-conical portion 35 helps to separate the introducer sheath 20 as it is pulled proximally. Gripping area 33 helps to stabilize the slitter 31 during use.

After the introducer sheath 20 is completely removed from the patient 8, the pacing lead 86 is connected to a pacing systems analyzer and standard evaluation of lead position can be performed by testing pacing thresholds, sensing, and lead impedance. Minor position changes can be accomplished by manipulating the pacing lead 86 directly if necessary. After the pacing lead 86 is properly positioned, the permanent pacemaker set 88 is then attached and implanted in the patient 8 using standard pacemaker procedures.

Figure 18:
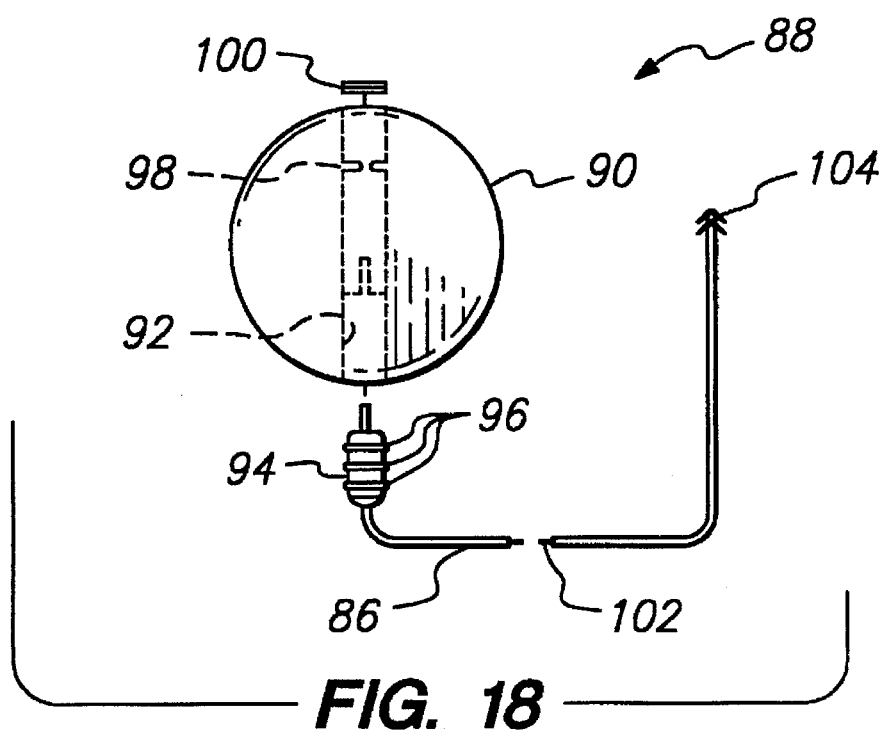
FIG. 18 is a plan view of a pacemaker set having a pacing lead.

The pacing lead 86 can be part of a permanent pacemaker set 88 such as the one that is illustrated in FIG. 18. Typically, pacing leads have a diameter of 4F to 11F (1.32 mm to 3.63 mm). However, the present invention could be down-sized to accommodate the placement of smaller diameter leads. The pacemaker set 88 has a pulse generator 90 comprising an electronic circuit and power supply encapsulated therein. The pulse generator 90 has a receptacle 92 for receiving a plug 94 of the pacing lead 86. The plug 94 has a plurality of ridges 96 which operate as O-rings to form a seal with the receptacle 92 when the plug 94 is inserted therein. The plug 94 is secured in the pulse generator 90 with vice screw 98. A cap 100 covers the end of the receptacle 92. A conductor 102 connects the plug 94 to a tined pacing lead tip 104. The tined leads are used to attach the pacing lead 86 to the tissue at the apex AP of the right ventricle RV.

Although a specific example of the permanent pacemaker set is described, it will be appreciated by one of ordinary skill in the art that the apparatus and method herein disclosed are not limited to such a pacemaker set. For example, the invention is compatible for use with multiple leads, temporary pacemaker lead placement, an integral or one-piece pulse generator and pacing lead or an active fixation lead can be used in place of the tined lead. It will also be appreciated by one of ordinary skill in the art that all dimensions for guidewires, dilators, sheaths, etc. are for example only and that the size of all components can be increased or decreased to fit specific needs.

Although the invention as described pertains to the introduction of permanent pacing leads into the right ventricle RV of the heart 14, other devices can be introduced into the right ventricle RV. Examples of other medical devices include, but are not limited to, leads for implantable defibrillation and/or anti-tachycardia pacing systems, temporary pacing leads, electrophysiology catheters, and mechanical devices such as bioptomes (biopsy forceps) used for performing right ventricular endomyocardial biopsies.

Modifications and variations of the present invention will be apparent to those having ordinary skill in the art having read the above teachings, and the present invention is thus limited only by the spirit and scope of the following claims.

What is claimed is:

1. A device for use in rapid, atraumatic placement of medical devices in a right ventricle of a patient comprising:

an introducer sheath used as a passage for transvenous placement of a medical device in a patient's heart, the introducer sheath being of sufficient length to allow a proximal end thereof to be located outwardly from an opening in the skin of the patient over the cephalic vein when a distal end of said introducer sheath is at an apex of the right ventricle, said introducer sheath having a gradient of stiffness which decreases toward the distal end so as to be sufficiently soft and flexible distally to pass atraumatically through a tricuspid valve and have sufficient strength proximally to allow the introducer sheath to be pushed along the length thereof through a tortuous venous path to the apex of the right ventricle;

said introducer sheath having an inside diameter of sufficient size to slidably receive a balloon-tipped catheter or pacing lead therethrough.

2. The device of claim 1 further comprising:

a balloon-tipped catheter within said introducer sheath.

3. The device of claim 1 further comprising:

a radio opaque marker at the distal end of said introducer sheath.

4. The device of claim 1 further comprising:

at least one radio opaque marker spaced from the distal end of said introducer sheath.

5. The device of claim 1 wherein said introducer sheath is radio opaque along at least a portion of its length.

6. The device of claim 1 further comprising:

a groove extending along said introducer sheath to weaken said introducer sheath to allow said introducer sheath to be split apart.

7. The device of claim 1 further comprising:

a plurality of perforations extending along said introducer sheath to weaken said introducer sheath to allow said introducer sheath to be peeled away.

8. The device of claim 1 further comprising:

a flange attached to the proximal end of said introducer sheath.

9. The device of claim 8 further comprising:

a dilator having a tapered distal end, a central bore of sufficient size to pass a guide member therethrough, and being of sufficient length to extend from a proximal end located at a point beyond said proximal end of said introducer sheath past the distal end of said introducer sheath;

said introducer sheath having an inside diameter configured for a close fit of said dilator in said introducer sheath.

10. The device of claim 9 further comprising:

a clip attached to the proximal end of said dilator for detachably mating with said flange attached to the proximal end of said introducer sheath to prevent separation of said dilator and introducer sheath during manipulation.

11. The device of claim 10 further comprising:

a slitter for slitting said introducer sheath longitudinally from the proximal end to the distal end upon withdrawal of said introducer sheath from the patient.

12. The device of claim 9 wherein the gradient of stiffness comprises one of the following: a wall thickness of the introducer sheath which decreases from the proximal end to the distal end; a wall thickness of the introducer sheath which decreases along at least a portion of its length; an outside diameter of the introducer sheath which decreases from the proximal end to the distal end while the inside diameter of the introducer sheath remains constant; an outside diameter of the introducer sheath which decreases along at least a portion of its length while the inside diameter of the introducer sheath remains constant; stiffness which varies along the length of the introducer sheath from the proximal end to the distal end; stiffness which varies along at least a portion of the introducer sheath; stiffness which varies gradually; stiffness which varies in one incremental step; stiffness which varies in a plurality of steps; a material of varying density; a material of varying polymer or metal composition mixture; and a material having a varied degree of cross-linking.

13. The device of claim 12 wherein the dilator varies in stiffness along at least a portion of its length.

14. The device of claim 1 wherein said length of said introducer sheath is at least 40 cm.

15. The device of claim 1 wherein the inside of said introducer sheath is a low-friction surface.

16. The device of claim 1 wherein said inside diameter of said introducer sheath is at least 1.65 mm.

17. The device of claim 1 wherein said introducer sheath has a length sufficient to extend from the apex of the right ventricle to outwardly of an incision over the cephalic vein on the patient's right side.

18. The device of claim 1 wherein said introducer sheath has a length sufficient to extend from the apex of the right ventricle to outwardly of an incision over the cephalic vein on the patient's left side.

19. The device of claim 1 wherein a distal portion of the introducer sheath that extends from the superior vena cava to an area in the vicinity of the apex of the right ventricle is soft and flexible.

20. A device for use in rapid, atraumatic placement of medical devices in a right ventricle of a patient comprising:

an introducer sheath used as a passage for transvenous placement of a medical device in a patient's heart, said introducer sheath being of sufficient length to allow a proximal end thereof to be located outwardly from an opening in the skin of the patient over the cephalic vein when a soft and flexible distal end of said introducer sheath is at an apex of the right ventricle, said introducer sheath having sufficient flexibility to pass atraumatically through a tricuspid valve and having sufficient strength to allow the introducer sheath to be pushed along the length thereof through a tortuous venous path to the apex of the right ventricle;

said introducer sheath having a gradient of stiffness which decreases toward the distal end along at least a portion of its length and an inside diameter of sufficient size to pass a removable flexible guidewire therethrough.

21. The device of claim 20 further comprising:

a removable flexible guidewire slidably received in said introducer sheath.

22. The device of claim 21 wherein said removable flexible guidewire is an angled, J-tipped guidewire.

23. The device of claim 20 further comprising:

a radio opaque marker at the distal end of said introducer sheath.

24. The device of claim 20 further comprising:

at least one radio opaque marker spaced from the distal end of said introducer sheath.

25. The device of claim 20 wherein said introducer sheath is radio opaque along at least a portion of its length.

26. The device of claim 20 further comprising:

a groove extending along said introducer sheath to weaken said introducer sheath to allow said introducer sheath to be split apart.

27. The device of claim 20 further comprising:

a plurality of perforations extending along said introducer sheath to weaken said introducer sheath to allow said introducer sheath to be peeled away.

28. The device of claim 20 further comprising:

a flange attached to the proximal end of said introducer sheath.

29. The device of claim 28 further comprising:

a dilator having a tapered distal end, a central bore of sufficient size to pass said guidewire therethrough, and being of sufficient length to extend from a proximal end located at a point beyond said proximal end of said introducer sheath past the distal end of said introducer sheath;

said introducer sheath having an inside diameter configured for a close fit of said dilator in said introducer sheath.

30. The device of claim 29 further comprising: a clip attached to the proximal end of said dilator for detachably mating with said flange attached to the proximal end of said introducer sheath to prevent separation of said dilator and introducer sheath during manipulation.

31. The device of claim 29 further comprising:

a slitter for slitting said introducer sheath longitudinally from the proximal end to the distal end upon withdrawal of said introducer sheath from the patient.

32. The device of claim 29 wherein the dilator varies in stiffness along at least a portion of its length.

33. The device of claim 20 wherein said length of said introducer sheath is at least 40 cm.

34. The device of claim 20 wherein the inside of said introducer sheath is a low-friction surface.

35. The device of claim 20 wherein said inside diameter of said introducer sheath is at least 0.66 mm.

36. The device of claim 20 wherein said introducer sheath has a length sufficient to extend from the apex of the right ventricle to outwardly of an incision over the cephalic vein on the patient's right side.

37. The device of claim 20 wherein said introducer sheath has a length sufficient to extend from the apex of the right ventricle to outwardly of an incision over the cephalic vein on the patient's left side.

38. The device of claim 20 wherein the varying stiffness comprises one of the following: a wall thickness of the introducer sheath which decreases from the proximal end to the distal end; an outside diameter of the introducer sheath which decreases from the proximal end to the distal end while the inside diameter of the introducer sheath remains constant; stiffness which varies gradually; stiffness which varies in one incremental step; stiffness which varies in a plurality of steps; a material of varying density; a material of varying polymer or metal composition mixture; and a material having a varied degree of cross-linking.

39. The device of claim 20 wherein a distal portion of the introducer sheath that extends from the superior vena cava to an area in the vicinity of the apex of the right ventricle is soft and flexible.

40. A kit for rapid, atraumatic right ventricular placement of medical devices comprising:

a guide member;

a dilator having a tapered distal end and a central bore of sufficient size for passing the guide member therethrough; and an introducer sheath used as a passage for transvenous placement of a medical device in a patient's heart, said introducer sheath being of sufficient length to allow a proximal end thereof to be located outwardly from an opening in the skin of the patient over the cephalic vein when a distal end is at an apex of the right ventricle, said introducer sheath having a gradient of stiffness which decreases toward the distal end so as to be sufficiently soft and flexible distally to pass atraumatically through a tricuspid valve and have sufficient strength proximally to allow the introducer sheath to be pushed along the length thereof through a tortuous venous path to the apex of the right ventricle, and having an inside diameter configured for a close fit of said dilator therein;

said dilator having a length greater than the length of the introducer sheath.

41. The kit of claim 40 further comprising:

a flange on the proximal end of said introducer sheath; and a clip attached to a proximal end of said dilator for detachably mating with said flange of said introducer sheath to prevent separation of said dilator and introducer sheath during manipulation.

42. The kit of claim 41 further comprising a balloon-tipped catheter sized to fit within said introducer sheath.

43. The kit of claim 41 further comprising:

at least one radio opaque marker spaced from the distal end of said introducer sheath.

44. The kit of claim 40 wherein said guide member is a flexible guidewire.

45. The kit of claim 44 wherein said flexible guidewire is angled and J-tipped.

46. The kit of claim 40 further comprising a hollow needle having an inside diameter sufficient to pass said guide member therethrough.

47. The kit of claim 40 further comprising a permanent pacemaker set.

48. The kit of claim 40 further comprising:

a radio opaque marker at the distal end of said introducer sheath.

49. The kit of claim 40 wherein said introducer sheath is radio opaque along at least a portion of its length.

50. The kit of claim 40 further comprising:

a groove extending along said introducer sheath to weaken said introducer sheath to allow said introducer sheath to be split apart.

51. The kit of claim 40 further comprising:

a plurality of perforations extending along said introducer sheath to weaken said introducer sheath to allow said introducer sheath to be peeled away.

52. The kit of claim 40 further comprising:

a slitter for slitting said introducer sheath longitudinally from the proximal end to the distal end upon withdrawal of said introducer sheath from the patient.

53. The kit of claim 40 wherein the gradient of stiffness comprises one of the following: a wall thickness of the introducer sheath which decreases from the proximal end to the distal end; a wall thickness of the introducer sheath which decreases along at least a portion of its length; an outside diameter of the introducer sheath which decreases from the proximal end to the distal end while the inside diameter of the introducer sheath remains constant; an outside diameter of the introducer sheath which decreases along at least a portion of its length while the inside diameter of the introducer sheath remains constant; stiffness which varies along the length of the introducer sheath from the proximal end to the distal end; stiffness which varies along at least a portion of the introducer sheath; stiffness which varies gradually; stiffness which varies in one incremental step; stiffness which varies in a plurality of steps; a material of varying density; a material of varying polymer or metal composition mixture; and a material having a varied degree of cross-linking.

54. The kit of claim 40 wherein the dilator varies in stiffness along at least a portion of its length.

55. The kit of claim 40 wherein said guide member is a balloon-tipped catheter sized to fit within said introducer sheath.

56. The kit of claim 40 further comprising a flexible guidewire.

57. The kit of claim 56 wherein said flexible guidewire is angled and J-tipped.

58. The kit of claim 40 wherein a distal portion of the introducer sheath that extends from the superior vena cava to an area in the vicinity of the apex of the right ventricle is soft and flexible.

59. A method for rapid, atraumatic right ventricular placement of medical devices across a tricuspid valve to an apex of a right ventricle in the heart of a patient comprising:

providing a guide member and a hollow needle having an inside diameter sufficient to pass said guide member therethrough;

providing an introducer sheath used for transvenous placement of a medical device in a patient's heart, said introducer sheath being of sufficient length to allow a proximal end thereof to be located outwardly from an opening in the skin of the patient over the cephalic vein when a distal end is at an apex of the right ventricle, said introducer sheath having a gradient of stiffness which decreases toward the distal end so as to be sufficiently soft and flexible distally to pass atraumatically through a tricuspid valve and have sufficient strength proximally to allow the introducer sheath to be pushed along the length thereof through a tortuous venous path to the apex of the right ventricle, and having an inside diameter of sufficient size to pass said guide member therethrough;

inserting said needle into a vein of the patient;

passing said guide member through said needle into the vein and into a superior vena cava;

removing said needle;

advancing said guide member across the tricuspid valve to a vicinity of the apex of the right ventricle; and advancing the introducer sheath over said guide member across the tricuspid valve into the vicinity of the apex of the right ventricle.

60. The method of claim 59 wherein said vein is a cephalic vein.

61. The method of claim 59 wherein said vein is a subclavian vein.

62. The method of claim 59 wherein said guide member is a flexible guidewire.

63. The method of claim 62 further comprising removing said flexible guidewire.

64. The method of claim 63 wherein said flexible guidewire is angled and J-tipped.

65. The method of claim 59 wherein:
said guide member comprises a balloon-tipped catheter;
said method further comprises:
advancing said balloon-tipped catheter in said introducer sheath until a distal end of said balloon-tipped catheter exits the distal end of said introducer sheath in proximity to the tricuspid valve;
inflating a balloon on the distal end of said balloon-tipped catheter;
advancing said balloon-tipped catheter across the tricuspid valve to the apex of the right ventricle; and
advancing said introducer sheath over said balloon-tipped catheter across the tricuspid valve into the vicinity of the apex of the right ventricle and deflating said balloon.

66. The method of claim 59 further comprising:
providing a dilator having a taper at a distal end, a central bore of sufficient size for passing the guide member therethrough, an outside diameter configured for a close fit of said dilator in said introducer sheath, and having a length greater than the length of said introducer sheath;
positioning said dilator fully in said introducer sheath so that the taper at the distal end of said dilator extends past said distal end of said introducer sheath;
sliding said dilator and said introducer sheath together over said guide member through the subclavian vein into the superior vena cava; and
removing said dilator from the superior vena cava.

67. The method of claim 59 further comprising:
providing a permanent pacemaker set having a ventricular pacing lead;
inserting said ventricular pacing lead into said introducer sheath;
advancing said ventricular pacing lead through said introducer sheath to the distal end of said introducer sheath;
removing said introducer sheath;
attaching said ventricular pacing lead to the apex of the right ventricle;
connecting said ventricular pacing lead to said permanent pacemaker set; and
implanting said permanent pacemaker set into the patient.

68. The method of claim 67 wherein:
said introducer sheath further comprises a groove extending along said introducer sheath to weaken said introducer sheath to allow said introducer sheath to be split apart; and the method further comprising removing said introducer sheath by withdrawing said introducer sheath over said ventricular pacing lead and splitting said introducer sheath apart along said groove.

69. The method of claim 67 wherein:
said introducer sheath further comprises a plurality of perforations extending along said introducer sheath to weaken said introducer sheath to allow said introducer sheath to be peeled away; and the method further comprising, removing said introducer sheath by withdrawing said introducer sheath over said ventricular pacing lead and peeling said introducer sheath apart along said perforations.

70. The method of claim 67 further comprising:
providing a slitter for slitting said introducer sheath longitudinally from the proximal end to the distal end upon withdrawal of said introducer sheath from the patient; and the method further comprising, removing said introducer sheath by withdrawing said introducer sheath over said ventricular pacing lead and slitting said introducer sheath apart with the slitter.

71. The method of claim 59 wherein said needle is inserted into the vein on the patient's right side.

72. The method of claim 59 wherein said needle is inserted into the vein on the patient's left side.

73. The method of claim 59 further comprising:

making an incision in the skin of the patient; and inserting the needle through the incision and into the vein of the patient.

74. A method for rapid, atraumatic right ventricular placement of medical devices across a tricuspid valve to an apex of a right ventricle in the heart of a patient comprising:

providing a balloon-tipped catheter and a hollow needle having an inside diameter sufficient to pass said balloon-tipped catheter therethrough;

providing an introducer sheath used for transvenous placement of a medical device in a patient's heart, said introducer sheath being of sufficient length to allow a proximal end thereof to be located outwardly from an opening in the skin of the patient over the cephalic vein when a distal end is at an apex of the right ventricle, said introducer sheath having a gradient of stiffness which decreases toward the distal end so as to be sufficiently soft and flexible distally to pass atraumatically through a tricuspid valve and have sufficient strength proximally to allow the introducer sheath to be pushed along the length thereof through a tortuous venous path to the apex of the right ventricle, and having an inside diameter of sufficient size to pass said balloon-tipped catheter therethrough;

inserting said needle into a vein of the patient;

passing said balloon-tipped catheter through said needle into the vein and into a superior vena cava;

removing said needle;

advancing said balloon-tipped catheter in said introducer sheath until a distal end of said balloon-tipped catheter exits the distal end of said introducer sheath in proximity to the tricuspid valve;

inflating a balloon on the distal end of said balloon-tipped catheter;

advancing said balloon-tipped catheter across the tricuspid valve to a vicinity of the apex of the right ventricle;

advancing said introducer sheath over said balloon-tipped catheter across the tricuspid valve into a position adjacent the inflated balloon;

deflating said balloon; and withdrawing the balloon-tipped catheter.

* * * * *